United States Patent
Tanaka et al.

(10) Patent No.: US 11,624,120 B2
(45) Date of Patent: Apr. 11, 2023

(54) ADDITIVE FOR ELECTROLYTIC PLATING SOLUTIONS, ELECTROLYTIC PLATING SOLUTION CONTAINING ADDITIVE FOR ELECTROLYTIC PLATING SOLUTIONS, AND ELECTROLYTIC PLATING METHOD USING ELECTROLYTIC PLATING SOLUTION

(71) Applicant: ADEKA CORPORATION, Tokyo (JP)

(72) Inventors: Shinichi Tanaka, Tokyo (JP); Shouhei Toyoda, Tokyo (JP); Shinya Ishiwata, Tokyo (JP); Takuya Takahashi, Jeonrabukdo (KR); Yong Gyun Kim, Jeonrabukdo (KR)

(73) Assignee: ADEKA CORPORATION, Tokyo (JP)

( * ) Notice: Subject to any disclaimer, the term of this patent is extended or adjusted under 35 U.S.C. 154(b) by 333 days.

(21) Appl. No.: 16/641,869

(22) PCT Filed: Aug. 23, 2018

(86) PCT No.: PCT/JP2018/031139
§ 371 (c)(1),
(2) Date: Feb. 25, 2020

(87) PCT Pub. No.: WO2019/044651
PCT Pub. Date: Mar. 7, 2019

(65) Prior Publication Data
US 2020/0224324 A1 Jul. 16, 2020

(30) Foreign Application Priority Data
Aug. 31, 2017 (JP) .............................. JP2017-166424

(51) Int. Cl.
*C25D 3/38* (2006.01)
*C07C 237/10* (2006.01)
*C08G 83/00* (2006.01)

(52) U.S. Cl.
CPC .............. *C25D 3/38* (2013.01); *C07C 237/10* (2013.01); *C08G 83/003* (2013.01)

(58) Field of Classification Search
None
See application file for complete search history.

(56) References Cited

U.S. PATENT DOCUMENTS

2003/0155248 A1    8/2003  Dalman et al.

FOREIGN PATENT DOCUMENTS

| CN | 102634778 | 8/2012 |
| JP | 2007-327127 | 12/2007 |
| JP | 5809055 | 11/2015 |
| JP | 6142165 | 6/2017 |
| KR | 10-2015-0137075 | 12/2015 |
| WO | 2014/162875 | 10/2014 |

OTHER PUBLICATIONS

Berchmans et al. J. Solid State Electrochem '2012' 16:1527-1535 (Year: 2012).*
Wan et al. (J. Phys. Chem. C 2008, 112, 1335-1344). (Year: 2008).*
International Search Report dated Oct. 16, 2018 in International (PCT) Application No. PCT/JP2018/031139.

* cited by examiner

*Primary Examiner* — Wojciech Haske
(74) *Attorney, Agent, or Firm* — Wenderoth, Lind & Ponack, L.L.P.

(57) ABSTRACT

The present invention provides an additive for electrolytic plating solutions, containing at least one selected from compounds represented by the chemical formulas (1) to (4) given in the present description, an electrolytic plating solution containing the additive for electrolytic plating solutions, and an electrolytic plating method that uses the electrolytic plating solution.

4 Claims, 1 Drawing Sheet

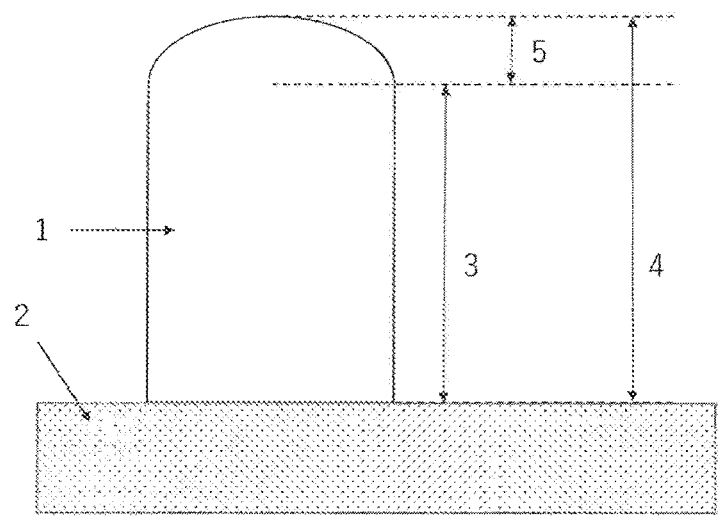

ADDITIVE FOR ELECTROLYTIC PLATING SOLUTIONS, ELECTROLYTIC PLATING SOLUTION CONTAINING ADDITIVE FOR ELECTROLYTIC PLATING SOLUTIONS, AND ELECTROLYTIC PLATING METHOD USING ELECTROLYTIC PLATING SOLUTION

TECHNICAL FIELD

The present invention relates to an additive for electrolytic plating solutions, containing a compound having a particular structure, to an electrolytic plating solution containing the additive for electrolytic plating solutions, and to an electrolytic plating method that uses the electrolytic plating solution.

BACKGROUND ART

Methods for filling metal into a pattern of, e.g., trenches, holes, and so forth, have been used to form the microscopic interconnects, TSVs, and bumps in highly integrated electronic circuits. Electrolytic plating is a typical metal filling method, and within this sphere electrolytic copper plating, which fills copper as the metal, is widely known. A problem with conventional electrolytic copper plating has been the occurrence of circuit continuity defects caused by a poor surface flatness for the filled copper layer. To provide a solution for this, for example, means have been investigated whereby copper is filled with a good surface flatness due to the action of an additive, e.g., a smoothing agent, that is introduced into the electrolytic copper plating solution.

Common smoothing agents used in electrolytic plating solutions can be exemplified by polyethyleneimine, polyaniline, polyacrylamide, polyvinylpyridine, polyvinylimidazole, polyvinylpyrrolidone, and polyacrylamide. For example, Patent Document 1 discloses polyvinylpyrrolidone as a smoothing agent for use in an aqueous copper electroplating solution for filling microfine copper interconnects. Patent Document 2 discloses polyethyleneimine as a smoothing agent for use in a copper plating solution for forming copper coating films, Patent Document 3 discloses polyethyleneimine as a smoothing agent for use in cyanide-free acidic silver plating baths.

CITATION LIST

Patent Documents

[Patent Document 1] Japanese Patent No. 5809055
[Patent Document 2] Japanese Patent No. 6142165
[Patent Document 3] Japanese Patent Application Laid-open No. 2007-327127

SUMMARY OF INVENTION

Technical Problem

However, the surface flatness of the metal layer has not been satisfactory in the case of metal layers formed by electrolytic plating methods using electrolytic plating solutions that contain a smoothing agent as described in Patent Documents 1 to 3. There is thus a requirement for an additive for electrolytic plating solutions capable of forming, by an electrolytic plating method, a metal layer having an excellent surface flatness.

Solution to Problem

As a result of extensive investigations, the present inventors discovered that the aforementioned problem can be solved by an additive for electrolytic plating solutions, containing a compound having a particular structure, an electrolytic plating solution containing the additive for electrolytic plating solutions, and an electrolytic plating method that uses the electrolytic plating solution, and achieved the present invention as a result.

Thus, the present invention relates to an additive for electrolytic plating solutions, containing at least one selected from the group consisting of compounds represented by chemical formulas (1) to (4).

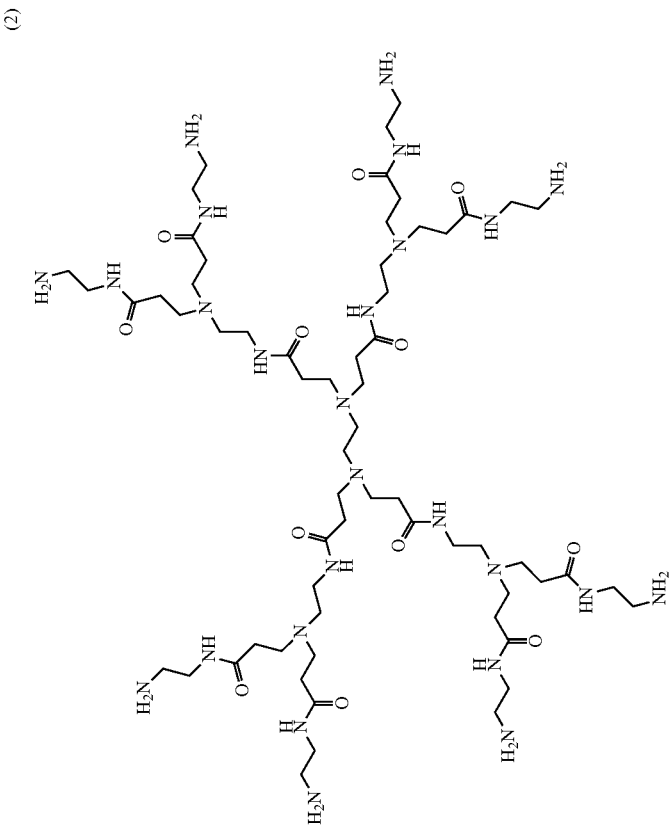
Compound No. 2
(2)
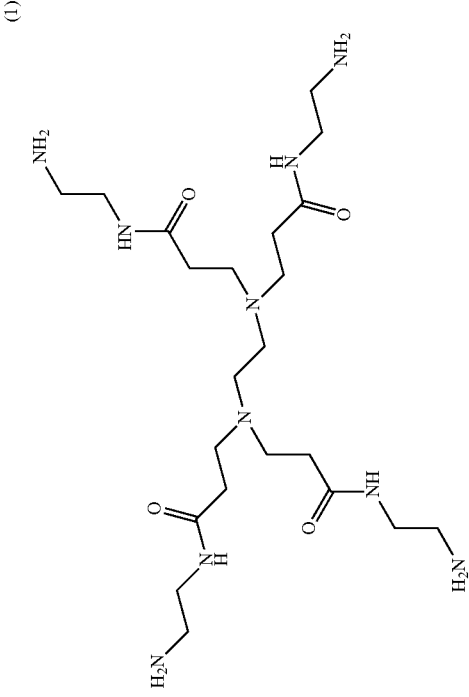
Compound No. 1
(1)

-continued
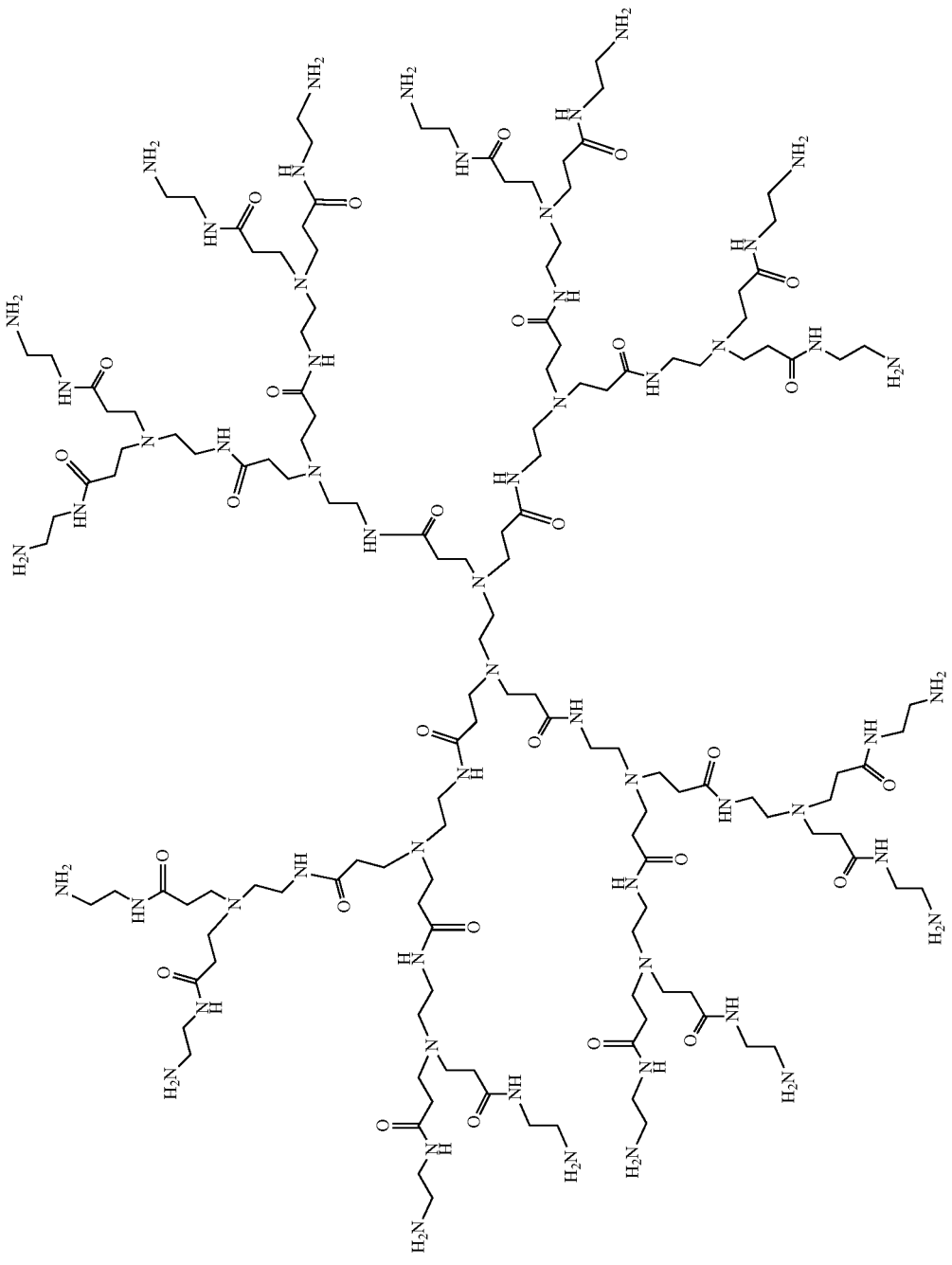
Compound No. 3

-continued
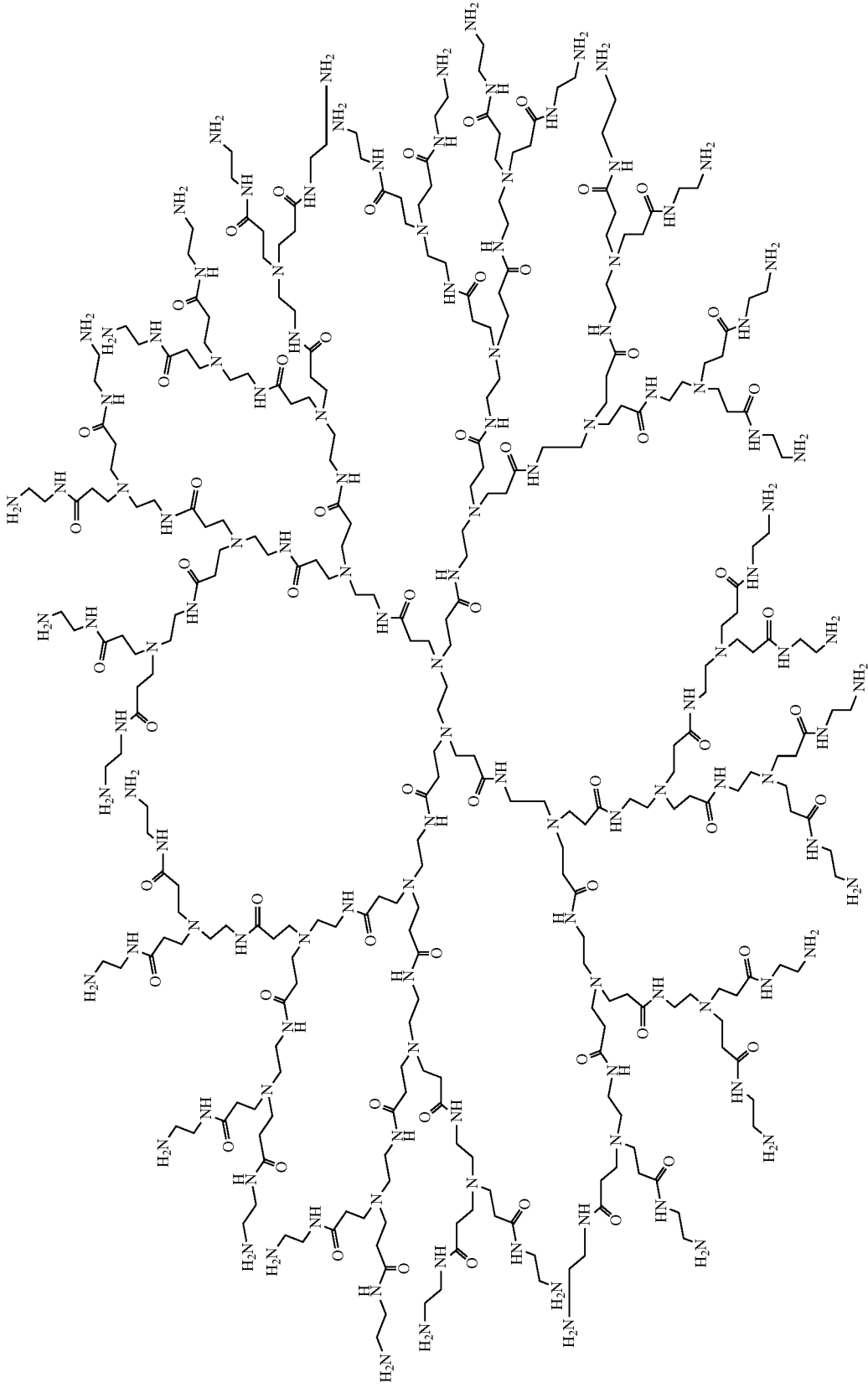
Compound No. 4

The present invention also provides an electrolytic plating solution containing the aforementioned additive for electrolytic plating solutions.

The present invention additionally provides an electrolytic plating method that uses the aforementioned electrolytic plating solution.

Advantageous Effects of Invention

When a process is carried out in which a metal layer is formed on a substrate using an electrolytic plating method that uses an electrolytic plating solution containing as an essential effective component the additive for electrolytic plating solutions according to the present invention, a metal layer can be filled with a good surface flatness into trenches and holes even when the surface of the substrate has a microfine structure. In addition, the additive for electrolytic plating solutions according to the present invention, when added to an electrolytic copper plating solution, can provide a very good surface flatness for the resulting copper layer and thus is particularly favorable as an additive for electrolytic copper plating solutions.

BRIEF DESCRIPTION OF DRAWINGS

FIG. 1 is a schematic diagram of a cross section of a plated substrate in an evaluation test, after the formation of a copper layer on the substrate surface by an electrolytic plating method.

DESCRIPTION OF EMBODIMENTS

<Additive for Electrolytic Plating Solutions>

The additive for electrolytic plating solutions according to the present invention contains at least one selected from the compounds No. 1 (product name: PAMAM dendrimer, ethylenediamine core, generation 0.0, Sigma-Aldrich, Inc.), No. 2 (product name: PAMAM dendrimer, ethylenediamine core, generation 1.0, Sigma-Aldrich, Inc.), No. 3 (product name: PAMAM dendrimer, ethylenediamine core, generation 2.0, Sigma-Aldrich, Inc.), and No. 4 (product name: PAMAM dendrimer, ethylenediamine core, generation 3.0, Sigma-Aldrich, Inc.) given by the preceding chemical formulas (1) to (4).

A metal layer having an excellent surface flatness can be formed when the metal layer is formed by an electrolytic plating method using an electrolytic plating solution that contains the additive for electrolytic plating solutions containing a compound as described above. Among the preceding, a metal layer having an even better surface flatness can be formed using an electrolytic plating solution that uses the additive for electrolytic plating solutions containing the aforementioned compound No. 1.

An even better surface flatness is exhibited when a metal layer is formed by an electrolytic plating method using an electrolytic plating solution that uses an additive for electrolytic plating solutions containing a particular alcohol compound and at least one selected from the aforementioned compounds No. 1 to 4, and this is thus preferred. Methanol, ethanol, n-propanol, and isopropanol are the particular alcohol compounds. Among these, the use of methanol is more preferred because this enables the formation of a metal layer having a particularly excellent surface flatness. These are used blended at, per 1 g of compound No. 1 to 4, preferably 0.1 g to 100 g and more preferably 1 g to 10 g.

<Electrolytic Plating Solution>

The electrolytic plating solution according to the present invention is described in the following. The electrolytic plating solution according to the present invention is an aqueous solution that contains, as an essential effective component, the additive for electrolytic plating solutions containing at least one selected from the aforementioned compounds No. 1 to 4. From the standpoint of obtaining the effects of the present invention to a more significant degree, the concentration thereof is preferably 0.1 mg/L to 100 mg/L, more preferably 0.5 mg/L to 50 mg/L, and still more preferably 1 mg/L to 30 mg/L.

With regard to components other than this additive for electrolytic plating solutions, the electrolytic plating solution according to the present invention may contain the same metal salt acting as a metal supply source, electrolyte, chloride ion source, plating accelerator, plating suppressor, and so forth as heretofore known electrolytic plating solutions.

The metal in the metal salt used in the electrolytic plating solution according to the present invention should be a metal with which a film can be formed by an electrolytic plating method, but is not otherwise particularly limited and can be exemplified by copper, tin, silver, and so forth. The surface flatness of the resulting copper layer is particularly excellent when the additive for electrolytic plating solutions according to the present invention is used in an electrolytic copper plating solution, which is thus preferred. The copper salt blended in the electrolytic copper plating solution can be exemplified by copper sulfate, copper acetate, copper fluoroborate, copper nitrate, and so forth.

The inorganic acid that is the electrolyte used in the electrolytic plating solution according to the present invention can be exemplified by sulfuric acid, phosphoric acid, nitric acid, hydrogen halides, sulfamic acid, boric acid, fluoroboric acid, and so forth.

The electrolytic plating solution according to the present invention, and particularly the copper plating solution based on copper sulfate and sulfuric acid, are advantageous because the resulting copper layer has a very good surface flatness. In this case, having the copper sulfate ($CuSO_4 \cdot 5H_2O$) be in the range of 10 g/L to 300 g/L and preferably 100 g/L to 250 g/L and the sulfuric acid be in the range of 20 g/L to 400 g/L and preferably 30 g/L to 150 g/L is efficient from the standpoint of the plating rate.

In addition, a chloride ion source may be used in the electrolytic plating solution according to the present invention in order to form a uniform and smooth metal layer. The chloride ion source is preferably blended at 5 mg/L to 200 mg/L in the electrolytic plating solution and is more preferably blended at 20 mg/L to 150 mg/L. There are no particular limitations on the chloride ion source, and, for example, NaCl, HCl, and so forth can be used.

A plating accelerator (brightener), e.g., an organic compound containing the element sulfur, salt compounds thereof, and so forth, may also be blended in the electrolytic plating solution according to the present invention. Compounds represented by the following general formulas (1) to (3) are plating accelerators.

$$XO_3S-R-SH \tag{1}$$

$$XO_3-Ar-S-S-Ar-SO_3X \tag{2}$$

(In the formulas of general formulas (1) and (2), R is an optionally substituted alkyl group and is preferably an alkyl group having from 1 to 6 carbons and is more preferably an alkyl group having from 1 to 4 carbons; Ar is an optionally substituted aryl group, for example, an optionally substituted phenyl group or naphthyl group; and X is a counterion, for example, sodium or potassium.)

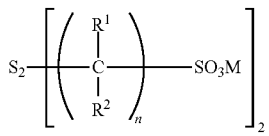

(In the formula, $R^1$ and $R^2$ are a hydrogen atom, a liner or branched alkyl group having 1 to 6 carbons, a cycloalkyl group having 5 to 9 carbons and possibly having a substituent having 1 to 3 carbons, or an aryl group possibly having a substituent having 1 to 3 carbons; M represents an alkali metal, ammonium, or a monovalent organoammonium; and n represents a number from 1 to 7.)

Among the preceding, sodium 3,3'-dithiobis(1-propanesulfonate) (also referred to as SPS in the following) is preferred for the plating accelerator because it has a strong accelerating effect on metal layer formation.

The concentration of the plating accelerator in the electrolytic plating solution is preferably 0.1 mg/L to 100 mg/L, more preferably 0.5 mg/L to 50 mg/L, and still more preferably 1 mg/L to 30 mg/L.

A plating suppressor is preferably also blended in the electrolytic plating solution according to the present invention. For example, an oxygen-containing polymeric organic compound can be used as the plating suppressor. Specific examples are polyethylene glycols, polypropylene glycols, polyoxyethylene-polyoxypropylene random copolymers, and polyoxyethylene-polyoxypropylene block copolymers, whereamong polyethylene glycols are preferred. From the standpoint of obtaining a substantial expression of the effects of the present invention, the molecular weight of this oxygen-containing polymeric organic compound is preferably 500 to 100,000 and is more preferably 1,000 to 10,000. In particular, a polyethylene glycol with a molecular weight of 1,000 to 10,000 is most preferred. Viewed from the same standpoint, the concentration of the oxygen-containing polymeric organic compound in the electrolytic plating solution is preferably 20 mg/L to 5,000 mg/L and is more preferably 50 mg/L to 3,000 mg/L.

Other additives known to be addable to plating solutions can optionally be used in the electrolytic plating solution according to the present invention within a range in which the purpose of the present invention is not compromised.

These other additives can be exemplified by anthraquinone derivatives, cationic surfactants, nonionic surfactants, anionic surfactants, amphoteric surfactants, alkanesulfonic acids, alkanesulfonate salts, alkanesulfonate esters, hydroxyalkanesulfonic acids, hydroxyalkanesulfonate salts, hydroxyalkanesulfonate esters, hydroxyalkanesulfonic acid/ organic acid esters, and so forth. The concentration of these additives in the electrolytic plating solution is preferably 0.1 mg/L to 500 mg/L and more preferably 0.5 mg/L to 100 mg/L.

<Electrolytic Plating Method>

The electrolytic plating method using the electrolytic plating solution according to the present invention is described in the following.

The electrolytic plating method according to the present invention may be carried out like a conventional electrolytic plating method, with the exception that the electrolytic plating solution according to the present invention is used as the electrolytic plating solution. An electrolytic copper plating method that forms a copper layer on a substrate to be plated is described here.

For example, a paddle-stirred plating apparatus is used as the electrolytic plating apparatus, and the substrate to be plated is immersed in an electrolytic copper plating bath provided by filling the electrolytic copper plating solution according to the present invention into the plating tank. The substrate to be plated is, for example, provided by the formation, using a photoresist, of a resist pattern on an Si substrate bearing a copper seed layer.

In this case, for example, the temperature of the electrolytic copper plating bath is 10° C. to 70° C. and preferably 20° C. to 50° C. and the current density is in the range from 1 A/dm$^2$ to 70 A/dm$^2$, preferably from 2 A/dm$^2$ to 50 A/dm$^2$, and more preferably from 5 A/dm$^2$ to 30 A/dm$^2$. For example, air stirring, rapid liquid flow stirring, mechanical stirring by, e.g., stirring blades, and so forth, can be used as the method for stirring the electrolytic plating solution.

Under the conditions given in the preceding, a copper layer having an excellent surface flatness can be formed on the plated substrate through the filling of copper into the opening regions of the resist pattern.

There are no particular limitations on the products on which plating produced using the electrolytic plating method according to the present invention may be executed, and these can be exemplified by a broad range of products, for example, materials in the automotive industry (heat sinks, carburetor parts, fuel injectors, cylinders, various valves, internal engine components, and so forth), materials in the electronics industry (contacts, circuits, semiconductor packages, printed circuit boards, thin film resistors, capacitors, hard disks, magnetic articles, lead frames, nuts, magnets, resistors, stems, computer parts, electronic components, laser oscillation elements, optical memory elements, optical fibers, filters, thermistors, heating elements, high-temperature heating elements, varistors, magnetic heads, various types of sensors (gas, temperature, humidity, light, speed, and so forth), MEMS, and so forth), precision equipment (copier components, optical device components, watch parts, and so forth), aviation and ship materials (hydraulic equipment, screws, engines, turbines, and so forth), materials in the chemical industry (balls, gates, plugs, checks, and so forth), various types of molds, machine tool components, vacuum equipment components, and so forth. The electrolytic plating method according to the present invention is preferably used in particular for materials in the electronics industry where microfine patterns are required, whereamong use in the production of printed circuit boards and semiconductor packages, as represented by TSV formation, bump formation, and so forth, is more preferred with semiconductor packages being most preferred.

EXAMPLES

The present invention is described in additional detail in the following using examples and comparative examples. However, the present invention is in no way limited by the following examples, etc.

Example 1

An electrolytic copper plating solution with the composition given in Table 1 was prepared using an additive for electrolytic plating solutions that contained methanol and compound No. 1 as the smoothing agent. In Examples 1 to 3 and Comparative Examples 1 and 2, the solvent in the electrolytic copper plating solution was water, and the component concentrations were adjusted using water. In addition, the polyethylene glycol used in the examples and comparative examples had a weight-average molecular weight of 3,600 to 4,400. The weight-average molecular weight was measured by gel permeation chromatographic analysis using tetrahydrofuran as the solvent and using polystyrene as the standard sample.

Example 2

An electrolytic copper plating solution with the composition given in Table 1 was prepared using an additive for electrolytic plating solutions that used compound No. 1 as the smoothing agent and that did not contain methanol.

Example 3

An electrolytic copper plating solution with the composition given in Table 1 was prepared using an additive for electrolytic plating solutions that contained methanol and compound No. 4 as the smoothing agent.

TABLE 1

| Electrolytic copper plating solution | Example 1 | Example 2 | Example 3 |
| --- | --- | --- | --- |
| Smoothing agent compound (concentration) | Compound No. 1 (5 mg/L) | Compound No. 1 (5 mg/L) | Compound No. 4 (5 mg/L) |
| Methanol (mg/L) | 20 | 0 | 20 |
| Copper sulfate pentahydrate (g/L) | 160 | 160 | 160 |
| Sulfuric acid (g/L) | 140 | 140 | 140 |
| Hydrogen chloride (mg/L) | 50 | 50 | 50 |
| SPS (mg/L) | 10 | 10 | 10 |
| Polyethylene glycol (g/L) | 1 | 1 | 1 |

Comparative Example 1

An electrolytic copper plating solution with the composition given in Table 2 was prepared using an additive for electrolytic plating solutions that contained methanol and the comparative compound 1 indicated below as the smoothing agent.

Comparative compound 1

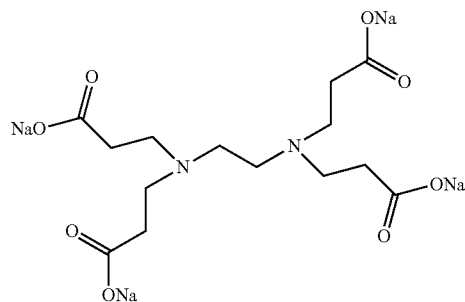

Comparative Example 2

An electrolytic copper plating solution with the composition shown in Table 2 was prepared using an additive for electrolytic plating solutions that contained methanol and the comparative compound 2 (polyethyleneimine (ethylenediamine branching), $M_w$ of approximately 800, Sigma-Aldrich, Inc.) indicated below as the smoothing agent.

Comparative compound 2

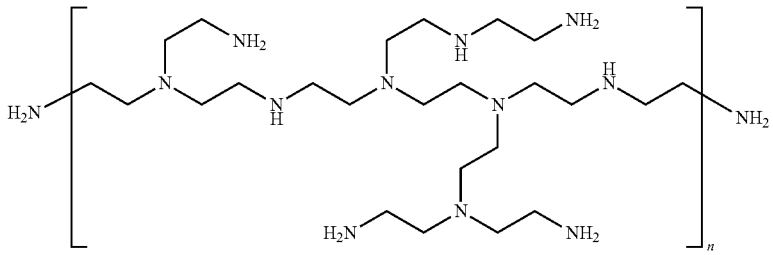

TABLE 2

| Electrolytic copper plating solution | Comparative Example 1 | Comparative Example 2 |
| --- | --- | --- |
| Smoothing agent compound (concentration) | Comparative compound 1 (5 mg/L) | Comparative compound 2 (5 mg/L) |
| Methanol (mg/L) | 20 | 20 |
| Copper sulfate pentahydrate (g/L) | 160 | 160 |
| Sulfuric acid (g/L) | 140 | 140 |
| Hydrogen chloride (mg/L) | 50 | 50 |
| SPS (mg/L) | 10 | 10 |
| Polyethylene glycol (g/L) | 1 | 1 |

Production Example 1

A paddle-stirred plating apparatus was used as the electrolytic plating apparatus. Electrolytic copper plating baths were prepared by filling the plating tank with, respectively, the electrolytic copper plating solutions of Examples 1 to 3 and Comparative Examples 1 and 2, and the substrate to be plated was immersed in each particular electrolytic copper plating bath. The substrate to be plated used here was prepared by forming, using a photoresist, a resist pattern (geometry: provided with opening regions with a circular cross section, opening diameters: 20 µm, 30 µm, and 50 µm) on an Si substrate bearing a copper seed layer. Then, under the plating conditions indicated below, copper was filled into the opening regions of the resist using each electrolytic copper plating method to form a copper layer on the plated substrate, (Plating Conditions)
(1) hole diameter (µm): 20, 30, 50
(2) current density (A/dm$^2$): 12, 16, 18
(3) bath temperature: 35° C.
(4) plating time: time required for the minimum height ($L_{min}$) of the plated copper layer to reach 40 µm Evaluation Example 1

The cross section of the copper layer 1 formed, as shown in FIG. 1, on the surface of the plated substrate 2 in accordance with Production Example 1 was observed using a laser microscope (model number: VK-9700, Keyence Corporation), and the minimum height ($L_{min}$) and the maximum height ($L_{Max}$) of the copper layer 1 were measured, ΔL was calculated using the following formula. The results of the evaluations are given in Table 3.

$$\Delta L = L_{Max} - L_{min}$$

Smaller values of ΔL in Table 3 indicate that a copper layer having a better surface flatness could be formed. Based on the results in Table 3, it was demonstrated that copper layer formation by the electrolytic plating methods that used the electrolytic copper plating solutions prepared in Examples 1 to 3, gave smaller values for ΔL than for the use of the electrolytic copper plating solution prepared in Comparative Example 1, and thus that the former were able to form copper layers having an excellent surface flatness. There was distortion in the shape of the surface of the copper layer formed using the electrolytic copper plating solution of Comparative Example 2 and ΔL could not be calculated.

In addition, when the use of the electrolytic plating solution of Example 1, which contained compound No. 1 (Evaluation Examples 1-1 to 1-3), is compared with the use of the electrolytic plating solution of Example 3, which contained compound No. 4 (Evaluation Examples 1-7 to 1-9), the values of ΔL are found to be lower in Evaluation Examples 1-1 to 1-3, and it was thus demonstrated that a copper layer having an even better surface flatness could be formed when the additive for electrolytic plating solutions containing compound No. 1 was added to the electrolytic copper plating solution.

Evaluation Examples 1-1 to 1-3, which used the electrolytic plating solution of Example 1 that contained compound No. 1 and methanol, gave smaller values of ΔL than Evalu-

TABLE 3

| | Electrolytic copper plating solution | Hole diameter (µm) | Current density (A/dm$^2$) | $L_{min}$ | $L_{Max}$ | ΔL |
|---|---|---|---|---|---|---|
| Evaluation Example 1-1 | Example 1 | 50 | 18 | 40.1 | 41.5 | 1.4 |
| Evaluation Example 1-2 | | 30 | 16 | 40.4 | 41.8 | 1.4 |
| Evaluation Example 1-3 | | 20 | 12 | 39.8 | 41.0 | 1.2 |
| Evaluation Example 1-4 | Example 2 | 50 | 18 | 40.5 | 43.6 | 3.1 |
| Evaluation Example 1-5 | | 30 | 16 | 39.7 | 42.7 | 3.0 |
| Evaluation Example 1-6 | | 20 | 12 | 40.2 | 41.9 | 1.7 |
| Evaluation Example 1-7 | Example 3 | 50 | 18 | 39.5 | 42.7 | 3.2 |
| Evaluation Example 1-8 | | 30 | 16 | 40.6 | 43.2 | 2.6 |
| Evaluation Example 1-9 | | 20 | 12 | 39.7 | 41.5 | 1.8 |
| Comparative Evaluation Example 1 | Comparative Example 1 | 50 | 18 | 40.3 | 51.4 | 11.1 |
| Comparative Evaluation Example 2 | | 30 | 16 | 40.6 | 48.6 | 8.0 |
| Comparative Evaluation Example 3 | | 20 | 12 | 40.1 | 45.2 | 5.1 |
| Comparative Evaluation Example 4 | Comparative Example 2 | 50 | 18 | (Could not be calculated due to shape distortion) | | |
| Comparative Evaluation Example 5 | | 30 | 16 | (Could not be calculated due to shape distortion) | | |
| Comparative Evaluation Example 6 | | 20 | 12 | (Could not be calculated due to shape distortion) | | | ation Examples 1-4 to 1-6, which used the electrolytic plating solution of Example 2, which contained compound No. 1 but did not contain methanol, and it could thus be confirmed that the copper layer exhibited an even better surface flatness by having the additive for electrolytic plating solutions contain methanol.

As has been described in the preceding, it was demonstrated that a copper layer having an excellent surface flatness can be formed when a copper layer is formed on a plated substrate by an electrolytic plating method that uses an electrolytic plating solution that uses an additive for electrolytic copper plating baths according to the present invention. More particularly, it could be confirmed that a copper layer having a particularly excellent surface flatness can be formed with the use of the additive for electrolytic copper plating solutions that contains compound No. 1 and methanol.

REFERENCE SIGNS LIST

1 Copper layer
2 Plated substrate
3 Minimum height ($L_{min}$)
4 Maximum height ($L_{Max}$)
5 ΔL

The invention claimed is:

1. An electrolytic plating solution comprising: a metal salt, an electrolyte and an additive for electrolytic plating solutions represented by chemical formula (1)

Compound No. 1

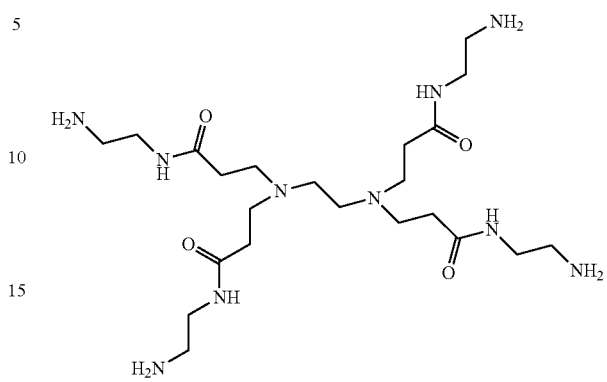

(1)

wherein the metal salt is copper sulfate and the electrolyte is sulfuric acid.

2. The electrolytic plating solution according to claim 1, comprising a chloride ion source.

3. The electrolytic plating solution according to claim 2, wherein the chloride ion source is hydrogen chloride.

4. An electrolytic plating method that uses the electrolytic plating solution according to claim 1, comprising
preparing a plating bath comprising the electrolytic plating solution;
immersing a substrate to be plated in the plating bath; and
forming a copper layer on the substrate.

* * * * *